(12) United States Patent
Karaolis

(10) Patent No.: US 7,291,465 B2
(45) Date of Patent: Nov. 6, 2007

(54) METHOD FOR DIRECT DETECTION OF FUNGAL PATHOGENS

(76) Inventor: David K. R. Karaolis, Oakhaven, Baltimore, MD (US) 21210

( * ) Notice: Subject to any disclaimer, the term of this patent is extended or adjusted under 35 U.S.C. 154(b) by 201 days.

(21) Appl. No.: 11/058,698

(22) Filed: Feb. 16, 2005

(65) Prior Publication Data

US 2007/0231793 A1    Oct. 4, 2007

Related U.S. Application Data

(60) Provisional application No. 60/545,895, filed on Feb. 20, 2004.

(51) Int. Cl.
*C12Q 1/68* (2006.01)
(52) U.S. Cl. .......................... 435/6; 435/91.1; 435/91.2
(58) Field of Classification Search .................. None
See application file for complete search history.

(56) References Cited

U.S. PATENT DOCUMENTS

| 5,580,971 | A | 12/1996 | Mitsuhashi |
| 5,707,802 | A | 1/1998 | Sandhu et al. |
| 5,753,467 | A | 5/1998 | Jensen et al. |
| 5,919,617 | A | 7/1999 | Bhattacharjee et al. |
| 6,387,652 | B1 | 5/2002 | Haugland et al. |
| 2002/0098487 | A1 | 7/2002 | Yokoyama et al. |
| 2003/0039981 | A1 | 2/2003 | Bhattacharjee et al. |
| 2003/0054369 | A1 | 3/2003 | Cruz-Perez et al. |
| 2003/0099946 | A1 | 5/2003 | Barnett et al. |
| 2003/0099975 | A1 | 5/2003 | Barnett et al. |

OTHER PUBLICATIONS

Zhou et al. Molecular and Cellular Probes vol. 14:339-348. 2000.*
Mahmoudi et al. Journal of Asthma vol. 37:191-198. 2000.*
Buck et al. Biotechniques. vol. 27:529-536. 1999.*

* cited by examiner

*Primary Examiner*—Teresa E. Strzelecka
*Assistant Examiner*—Heather Calamita
(74) *Attorney, Agent, or Firm*—Browdy & Neimark, PLLC

(57) ABSTRACT

The present invention relates to a method and diagnostic kit for directly detecting the presence of a specific species of mold/fungi in a sample, particularly a species which is toxic to humans or animals including pets and livestock. The method involves releasing any fungal DNA from the sample and subjecting it to PCR amplification without the need for purifying the DNA.

3 Claims, No Drawings

METHOD FOR DIRECT DETECTION OF FUNGAL PATHOGENS

CROSS-REFERENCE TO RELATED APPLICATIONS

The present application claims the benefit of priority under 35 U.S.C. § 119(e) from U.S. provisional application No. 60/545,895, filed Feb. 20, 2004, the entire content of which is hereby incorporated by reference.

BACKGROUND OF THE INVENTION

1. Field of the Invention

The present invention relates to the detection of fungi, particularly the detection of pathogenic fungi in building materials.

2. Description of the Related Art

The growth of fungi, such as certain types of black or gray molds in residential and commercial buildings, can produce significant health hazards to the human occupants thereof. For example, the black molds known as *Stachybotrys* and *Memnoniella* are types that are known to produce mycotoxins which are hazardous to human health upon exposure to these toxins. These mold types typically occur on repeatedly wetted materials that contain cellulose, for example, interior wall paneling, such as gypsum board, and other materials used in residential and commercial buildings including cardboard, ceiling tiles, cellulose insulation, wood, etc. See Andersson et al., 1997; Burge et al., 1999; Croft et al., 1986; Haugland et al., 1999; Leenders et al., 1999; Levetin, 1995; Sorenson et al., 1987; Stetzenbach, 1997; and Vesper et al., 2000; the entire contents and disclosures of each and all of which are incorporated herein by reference.

There are several sources of moisture which can accelerate and promote the growth of gray and black molds including the types mentioned above. Water piping extending through plumbing chases and piping extending through voids or spaces in interior walls of residential and commercial buildings can produce minute leaks sufficient to wet adjacent materials and promote the growth of mold. Leakage from the exterior of a building into various parts of the building, which goes undetected, can also wet the surfaces of various materials which would promote the growth of toxic molds. Still further, condensation, from time to time, on the surfaces of plumbing piping, air conditioning ducts, refrigerant conduits and other structures is also a source of moisture which can result in the growth of molds in unseen spaces, such as the interior wall spaces of buildings, among other locations, all of which are a source of mold contamination that humans are exposed to.

The growth of mold in interior wall spaces in residential and commercial buildings is particularly difficult to detect and difficult to eradicate by conventional methods. Since the interior wall spaces have been covered with various types of wall paneling, the growth of mold goes undetected and, when detected, is difficult to treat without major renovation of the building. Accordingly, there has been a longstanding need for the development of rapid and efficient mold detection methods and systems that will identify those areas in need of treatment to eradicate toxic mold infestations.

Methods are known for the quantitative determination of molds and fungal pathogens; however, such methods require the isolation and purification of genetic material (e.g., DNA) from the suspected fungi or the isolation of the mold and culturing thereof before analysis can take place.

U.S. Pat. No. 6,387,652 relates to the use of PCR or other molecular techniques to quantify the presence of fungi and bacteria; however, the methods disclosed require "extracting and recovering DNA" from the suspected organism.

Similarly, US application publication 20030054369 also requires the isolation and purification of the suspected DNA before quantitation thereof in the sample.

U.S. Pat. No. 5,580,971 discloses methods for the detection of particular genera or species of fungus in biological samples. The methods use a solid support-polynucleotide structure that includes a solid support having immobilized thereon a polynucleotide probe that is complementary to a sequence of ribosomal RNA (rRNA) specific to a particular species of fungus.

U.S. Pat. No. 5,707,802 discloses nucleic acid probes and primers for detecting fungi. The probes can detect rRNA, rDNA or polymerase chain reaction products from a majority of fungi in clinical, environmental or food samples. The methods disclosed all require the extraction and isolation of the nucleic acid from the suspected fungi.

U.S. Pat. No. 5,753,467 describes a method for the identification of fungi that requires first isolating DNA from the suspect material; the isolated DNA having variable sequences interspersed between highly conserved rDNA sequences. The variable sequences are amplified in such manner as to either amplify the variable sequences interspersed between highly conserved rDNA sequences or to amplify arbitrary genomic regions in conjunction with the variable sequences.

U.S. Pat. No. 5,919,617 describes methods and materials for detecting the presence of a fungus in biological samples.

US application publication 20020098487 discloses nucleic acids for detecting fungi that may be used as probes or primers for gene amplification and as primers for the detection and identification of fungi belonging to the genus *Aspergillus* in biological samples. Isolation of the target nucleic acid material is required.

US application publication 20030039981 provides a method and material for detecting the presence of a fungus in a biological sample. The method requires the isolation of the suspected DNA from the sample.

US application publication 20030099946 and US application publication 20030099975 relate to the use of primers in polymerase chain reaction assays for the detection of fungal pathogens *Colletotrichum acutatum*, *Alternaria* spp., and *Cladosporium carpophilum*. The methods require extracting and isolating DNA from an organism.

The above cited methods, however, are time consuming and expensive because they require the isolation and purification of the nucleic acids, thereby rendering them inefficient and inconvenient in situations where all that is required is a qualitative screening for the presence of the mold. The entire contents and disclosures of each and all of the above listed patents are incorporated herein by reference.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to provide a method and system that enables the quick and efficient qualitative identification and detection of the presence of molds and fungi, particularly the toxic molds and fungi that grow on building materials. The present method can be used to confirm the suspected contamination of such materials.

The present invention thus provides a method for detecting a specific species of fungi in a sample, such as a sample taken from building and construction material, using PCR amplification without the need for isolating or purifying away from other cell components (other than perhaps centrifuging away cell debris) any fungal DNA released in the sample.

The present invention also provides a diagnostic kit for the direct detection of a specific species of fungi in a sample.

DETAILED DESCRIPTION OF THE INVENTION

The present invention is directed to a method for detecting the presence of a specific species of fungi in a sample, involving releasing DNA from any fungi present in the sample and subjecting the released DNA directly to amplification by polymerase chain reaction (PCR) without purifying the DNA. The PCR amplification of any released fungal DNA is performed using as PCR primers at least one pair of primers specific for the species of fungi to be detected. The presence of the specific species of fungi is then detected by visualizing any PCR amplification product obtained (i.e., on gel electrophoresis) and determining whether or not the PCR amplification product obtained corresponds to the expected product from amplification of the DNA of the specific species of fungi with the at least one pair of primers.

While the sample for which the present method is used to detect a specific species of fungi is preferably obtained from building and construction material, it can also be obtained from other sources for which detection of a specific species of fungi may be useful and important. Samples may be obtained in a variety of ways, including for instance, swabbing a surface (i.e., with a sterile moistened cotton swab), sampling a material, taking an air sample (i.e., passing a sample volume of air through an air filter to trap spores), etc.

Building and construction materials (e.g., ceiling tile, sheetrock, etc.) that might be contaminated with pathogenic or toxic species of fungi are sampled to collect any fungal material such as spores and hyphae. The pathogenic/toxic species of fungi include those in the genera *Stachybotyrs*, *Aspergillus* and *Penicillium*, and more particularly include, but are not limited to, *Stachybotyrs chartarum*, *Stachybotyrs atra*, *Aspergillus versicolor*, *Aspergillus fumigatus*, *Penicillium spinulosum* and *Penicillium chrysogenum*. It will be appreciated by those of skill in the art that a sample to be tested according to the method of the present invention may be any species of fungi, even though for purposes of the present invention, the species is preferably a pathogenic or toxic species of fungi.

Any fungal material such as spores and hyphae collected on a swab material or a filter material (i.e., air filter) can be suspended in an appropriate volume of sterile diluent (e.g., water, nutrient media, buffer, etc.) by agitating the swab or filter material to create a suspension of any fungal material in the diluent. An aliquot of this suspension can be plated onto appropriate agar plates in order to obtain fungal cultures. This is an optional confirmatory test for identifying fungal species that can be done in parallel with the method of the present invention. It serves merely to confirm by morphology, etc., the identity of a specific fungal species detected by the method of the present invention because the growth of such fungal cultures is not conducive to rapid qualitative detection. The remainder of the suspension can then be processed by conventional techniques well known in the art, preferably by bead milling or bead beating to release DNA from fungi.

It will also be appreciated that the fungal material suspended in solution can be centrifuged and concentrated before being processed to release any fungal DNA.

An aliquot (or the entire sample) containing any fungal DNA released from fungal cells is then used as a template (either directly or following appropriate dilutions), without any isolation and/or purification of any fungal DNA other than possibly centrifuging to pellet out cell debris, in a PCR amplification reaction using primers specific for a species of fungi. PCR amplification conditions previously shown to be able to detect and amplify from crude preparations of template DNA can be used. PCR amplification on crude preparations have been successfully performed to detect, for example, the presence of Shiga-like toxin producing *E. coli* in primary fecal cultures (Paton et al., 1993); fruitflies and blood flukes (Greveding et al., 1996); *Chlamydia trachamatis* for genotyping in cervical scrapes (Lan et al., 1993); *E. coli* and *Shigella dysenteriae* in sewage and sludge (Tsai et al., 1993); mycobacteria in clinical specimens (Mangiapan et al., 1996); *Trypanosoma evansi* in crude blood (Wuyts et al., 1995); and sulfate-reducing bacteria in crude oil (Tanaka et al., 2002).

With regard to primer pairs which selectively amplify DNA only from the fungal species for which they are specific, many such primers are known in the art for various fungal species or can be readily determined with only routine experimentation. Non-limiting examples of pairs of primers specific for a particular species of fungi include SEQ ID NOs:1 and 2 (*Stachybotyrs chartarum*), SEQ ID NOs:3 and 4 (*Aspergillus versicolor*), SEQ ID NOs:5 and 6 (*Aspergillus fumigatus*), SEQ ID NOs:7 and 8 (*Penicillium spinulosum*), and SEQ ID NOs:9 and 10 (*Pencillium chrysogenum*). Multiple pairs of primers specific for the same species of fungi to be detected, or where each pair is specific for a different species of fungi to be detected, can be present in the same PCR amplification for detection of one or more different species of fungi. Thus, the present method encompasses amplification with multiple pairs of primers specific for several different species of fungi so that simultaneous detection of more than one species can be performed.

Product(s) obtained by PCR amplification can be detected by visualizing the product(s) as band(s) following agarose or polyacrylamide gel electrophoresis and staining with an appropriate dye. The identity and specificity of the PCR product(s) can be further optionally confirmed by sufficiently purifying the PCR product(s) so that DNA sequencing can be performed.

The present invention also provides a diagnostic kit for the direct detection of a specific species of fungi in a sample. This diagnostic kit includes (1) at least one pair of primers for amplifying DNA from a specific species of fungi and (2) a sample of the specific species of fungi to be detected provided in a separate compartment or container/vial to serve as a positive control. This diagnostic may optionally further include the reagents and enzymes for PCR; otherwise, such reagents and enzymes may be obtained separately from commercial suppliers.

Having now generally described the invention, the same will be more readily understood through reference to the following example which is provided by way of illustration and is not intended to be limiting of the present invention.

EXAMPLE

The following procedure may be employed to detect the presence of *Stachybotyrs chartarum* in a sample derived from a construction material:

The swab (or sample) is placed in a diluent such as 20% (w/v) nutrient media (prepared from Bacto Nutrient Broth according to manufacturer's directions) or water with or without 0.5% sodium dodecylsulfate (0.5% final concentration), and then homogenized by adding 0.1 mm Zirconia/Silica beads to give an approximately 50% sample/bead mixture. Afterwards, the sample is subjected to vigorous bead-beating/milling for several minutes to release fungal DNA from hyphae or spores. The sample may then be heated in a boiling water bath for 5-10 min, allowed to cool to room temperature and centrifuged for several minutes to pellet cell debris. The supernatent, can be used either directly or serially diluted in water or 20% nutrient media as a template for the PCR analysis.

| PCR Reaction Mixture | |
| --- | --- |
| Fungal sample | 10 ul |
| 10× PCR buffer | 5 ul |
| 50 mM $MgCl_2$ | 1.5 ul |
| 10 mM dNTP | 1 ul |
| Primer1 (40 pM) | 2 ul |
| Primer2 (40 pM) | 2 ul |
| Taq polymerase | 0.25 ul |
| Water | 28.25 ul |
| Total | 50 ul |

Primer1=StacF4: 5'-TCCCAAACCCTTATGTGAACC-3' (SEQ ID NO:1; U.S. Pat. No. 6,387,652).

Primer2=StacR5: 5'-GTTTGCCACTCAGAGAATACT-GAAA-3' (SEQ ID NO:2; U.S. Pat. No. 6,387,652).

The PCR reaction mixture is then placed in a PCR machine (thermocycler) and subjected to the following conditions: 95° C. for 3 min, then 35 cycles of 95° C. for 1 min, 52° C. for 1 min, 72° C. for 2 min followed by 1 cycle of 72° C. for 10 min. Following PCR, an aliquot of the reaction containing any amplified DNA material is removed and run on an agarose gel, stained appropriately (e.g., with ethidium bromide or a fluorescent dye) and any PCR amplified products, i.e., DNA fragments, are visualized and detected.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Andersson et al., Bacteria, molds, and toxins in water-damaged building materials, *Appl Environ Microbiol.* 63:387-93 (1997)

Burge et al., Fungi. J. Macher, H. A. Ammann, H. A. Burge, D. K. Milton, and P. R. Morey (eds), In *Bioaerosols*, Cincinnati (1999)

Croft et al., Airborne outbreak of trichothecene toxicosis. *Atmospheric Environment*, 20:549-552 (1986)

Grevelding et al., Direct PCR on fruitflies and blood flukes without prior DNA isolation, *Nucleic Acids Res.*, 24(20): 4100-1 (1996)

Haugland et al., Quantitative measurement of *Stachybotrys chartarum* conidia using real time detection of PCR products with the TaqMan™ fluorogenic probe system. *Mol Cell Probes.* 13:329-40 (1999)

Lan et al., Direct detection and genotyping of *Chlamydia trachomatis* in cervical scrapes by using polymerase chain reaction and restriction fragment length polymorphism analysis, *J. Clin Microbiol.*, 31(5):1060-5 (1993)

Leenders et al., Density and molecular epidemiology of *Aspergillus* in air and relationship to outbreaks of *Aspergillus* infection, *J Clin Microbiol*, 37:1752-7 (1999)

Levetin, E., Fungi, p. 87-120. In *H. Burge Bioaerosols* (ed.), Lewis Publishers, Boca Raton (1995)

Mangiapan et al., Sequence capture-PCR improves detection of mycobacterial DNA in clinical specimens, *Clin Microbiol.*, 34(5):1209-15 (1996)

Paton et al., Direct detection of *Escherichia coli* Shiga-like txin genes in primary fecal cultures by polymerase chain reaction, *J Clin Microbiol*, 31(11)3063-7 (1993)

Sorenson et al., Trichothecene mycotoxins in aerosolized conidia of *Stachybotrys atra, Appl Environ Microbiol,* 53:1370-5 (1987)

Stetzenbach, L. D, Introduction to aerobiology, p. 619-628. In *Manual of environmental microbiology* C. Hurst, 0. R. Knudsen, M. J. Mclnerney, L. D. Stetzenbach, and M. V. EWalter (eds), ASM Press, Washington D.C. (1997)

Tanaka et al., A highly selective direct method of detecting sulphate-reducing bacteria in crude oil, *Lett Appl Microbiol.*, 35 (3):242-6 (2002)

Tsai et al., Detection of *Escherichia coli* in sewage and sludge by polymerase chain reaction, *Appl Environ Microbiol.*, 59(2):353-7 (1993)

Vesper et al., Evaluation of *Stachybotrys chartarum* in the house of an infant with pulmonary hemorrhage: quantitative assessment before, during, and after remediation. *J Urban Health*, 77:68-85 (2000)

Wuyts et al., PCR amplification of crude blood on microscope slides in the diagnosis of *Trypanosoma evansi* infection in dairy cattle, *Ann Soc Belg Med Trop.*, 75(3): 229-37 (1995)

What is claimed is:

1. A method for detecting the presence of *Stachybotyrs chartarum* in a sample, comprising:

releasing DNA from any fungi present in the sample;

subjecting the released DNA directly to amplification by polymerase chain reaction (PCR) without purifying the DNA, wherein the PCR amplification of any released DNA is performed using at least one pair of primers specific for *Stachybotyrs chartarum*; and detecting the presence of *Stachybotyrs chartarum* by visualizing any PCR amplification product to determine whether or not the PCR amplification product corresponds to an expected product from amplification of the DNA of *Stachybotyrs chartarum* with said at least one pair of primers, wherein said at least one pair of primers comprises a pair of primers which comprises the nucleotide sequences of SEQ ID NOs:3 and 4.

2. The method of claim 1, wherein the sample is obtained from construction or building material.

3. The method of claim 1, wherein the sample is an air sample.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
tcccaaaccc ttatgtgaac c                                            21

<210> SEQ ID NO 2
<211> LENGTH: 25
<212> TYPE: DNA
<213> ORGANISM: Artificial
<220> FEATURE:
<223> OTHER INFORMATION: Synthetic

<400> SEQUENCE: 2
gtttgccact cagagaatac tgaaa                                        25

<210> SEQ ID NO 3
<211> LENGTH: 14
<212> TYPE: DNA
<213> ORGANISM: Artificial
<220> FEATURE:
<223> OTHER INFORMATION: Synthetic

<400> SEQUENCE: 3
cggcggggag ccct                                                    14

<210> SEQ ID NO 4
<211> LENGTH: 25
<212> TYPE: DNA
<213> ORGANISM: Artificial
<220> FEATURE:
<223> OTHER INFORMATION: Synthetic

<400> SEQUENCE: 4
ccattgaaag ttttgactga tttta                                        25

<210> SEQ ID NO 5
<211> LENGTH: 15
<212> TYPE: DNA
<213> ORGANISM: Artificial
<220> FEATURE:
<223> OTHER INFORMATION: Synthetic

<400> SEQUENCE: 5
gcccgccgtt tcgac                                                   15

<210> SEQ ID NO 6
<211> LENGTH: 24
<212> TYPE: DNA
```

-continued

```
<213> ORGANISM: Artificial
<220> FEATURE:
<223> OTHER INFORMATION: Synthetic

<400> SEQUENCE: 6
gttgttgaaa gttttaactg attc                                              24

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
gtaccttgtt gcttcggtgc                                                   20

<210> SEQ ID NO 8
<211> LENGTH: 32
<212> TYPE: DNA
<213> ORGANISM: Artificial
<220> FEATURE:
<223> OTHER INFORMATION: Synthetic

<400> SEQUENCE: 8
cgttgttgaa agttttaact tatttagttt at                                     32

<210> SEQ ID NO 9
<211> LENGTH: 15
<212> TYPE: DNA
<213> ORGANISM: Artificial
<220> FEATURE:
<223> OTHER INFORMATION: Synthetic

<400> SEQUENCE: 9
cgggcccgcc ttaac                                                        15

<210> SEQ ID NO 10
<211> LENGTH: 36
<212> TYPE: DNA
<213> ORGANISM: Artificial
<220> FEATURE:
<223> OTHER INFORMATION: Synthetic

<400> SEQUENCE: 10
gaaagtttta aataatttat attttcactc agagta                                 36
```